United States Patent [19]
Goldberg et al.

[11] Patent Number: 5,341,803
[45] Date of Patent: Aug. 30, 1994

[54] APPARATUS AND METHOD FOR MONITORING GASTRIC FLUID PH

[76] Inventors: Michael S. Goldberg, 964 Crest Rd., Del Mar, Calif. 92014; Charles R. Horres, Jr., 13071 Via Grimaldi, Del Mar, Calif. 92014

[21] Appl. No.: 81,468
[22] Filed: Jun. 22, 1993
[51] Int. Cl.$^5$ ............................................. A61B 5/00
[52] U.S. Cl. ................................. 128/632; 128/635
[58] Field of Search ..................... 128/632, 635, 637; 204/406, 407, 433, 409, 408

[56] References Cited

U.S. PATENT DOCUMENTS

| | | | |
|---|---|---|---|
| 2,168,867 | 8/1939 | George, 3rd | 128/635 |
| 3,908,657 | 9/1975 | Kowarski | 128/278 |
| 3,910,256 | 10/1975 | Clark et al. | 128/635 |
| 3,968,800 | 7/1976 | Vilasi | 128/343 |
| 3,982,546 | 9/1976 | Friend | 128/350 |
| 3,983,864 | 10/1976 | Sielaff | 128/2 |
| 4,265,249 | 5/1981 | Schindler et al. | 128/635 |
| 4,324,262 | 4/1982 | Hall | 128/756 |
| 4,381,011 | 4/1983 | Somers, 3rd | 128/635 |
| 4,502,482 | 3/1985 | DeLuccia | 128/207.15 |
| 4,571,240 | 2/1986 | Samson et al. | 604/96 |
| 4,655,214 | 4/1987 | Linder | 128/207.18 |
| 4,671,287 | 6/1987 | Fiddian-Green | 128/637 |
| 4,734,184 | 3/1988 | Burleigh et al. | 204/433 |
| 4,811,542 | 11/1989 | Schmidt et al. | 128/207.14 |
| 4,976,265 | 12/1990 | Falcial et al. | 125/634 |
| 5,021,044 | 6/1991 | Sharkawy | 604/53 |
| 5,158,083 | 10/1992 | Sacristan et al. | 128/632 |
| 5,167,623 | 12/1992 | Cianci et al. | 604/43 |

*Primary Examiner*—Lee S. Cohen
*Assistant Examiner*—Robert L. Nasser, Jr.
*Attorney, Agent, or Firm*—Nydegger & Associates

[57] ABSTRACT

A device and method for monitoring the pH value of the aspirated gastric fluid of a patient includes a monitor, a sensor assembly engageable with the monitor, and a collecting reservoir engageable with the sensor assembly. The sensor assembly includes a sensor which is moveable on a base member between a cleansing cavity, calibrating cavities, and a monitoring cavity. The monitor includes a suction generating member which is connectable with the patient, and a microprocessor which is connectable with the sensor of the sensor assembly. In the operation of the device, gastric contents from the patient are aspirated by the suction generating member into the monitoring cavity. There, the sensor generates a signal indicative of the pH value of the gastric contents which is transmitted to the microprocessor. Periodically, during operation, the sensor is moved to the cleansing cavity for cleaning and subsequent calibration by successive contact with pH 7 and pH 1 solutions in the calibrations cavities of the sensor assembly.

18 Claims, 3 Drawing Sheets

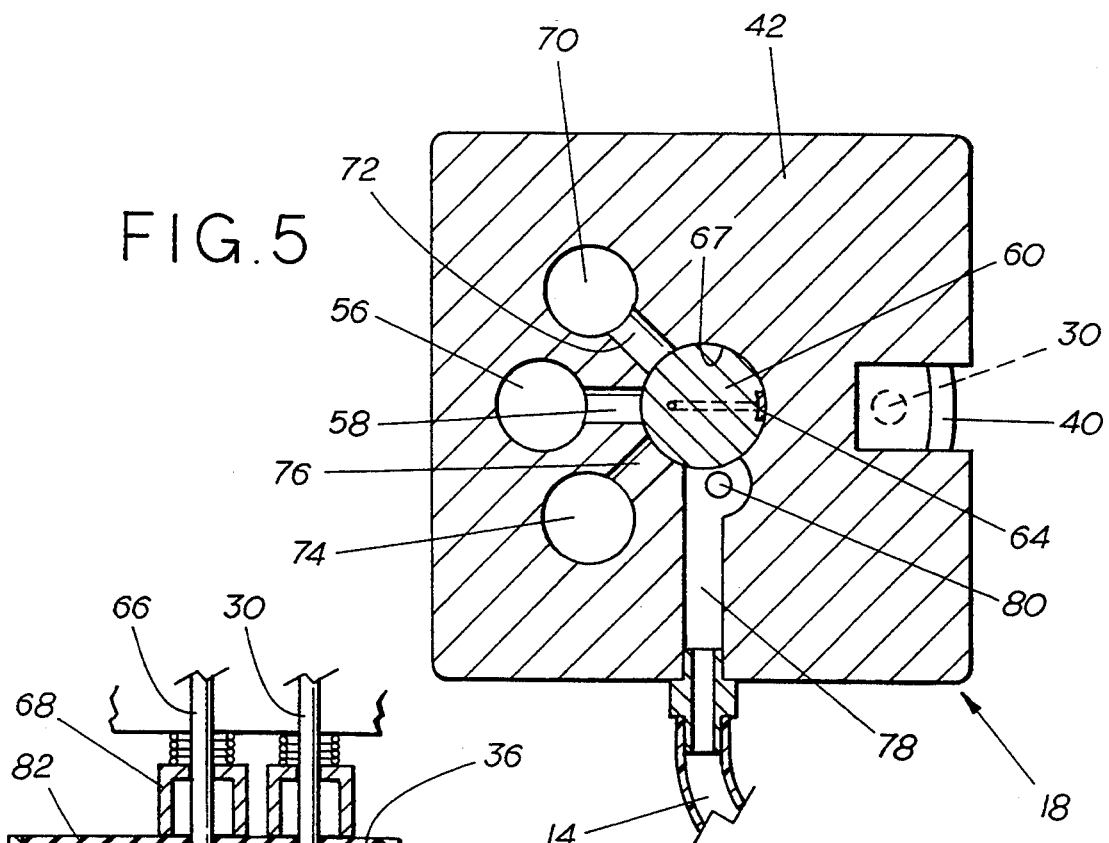
FIG.5
FIG.6
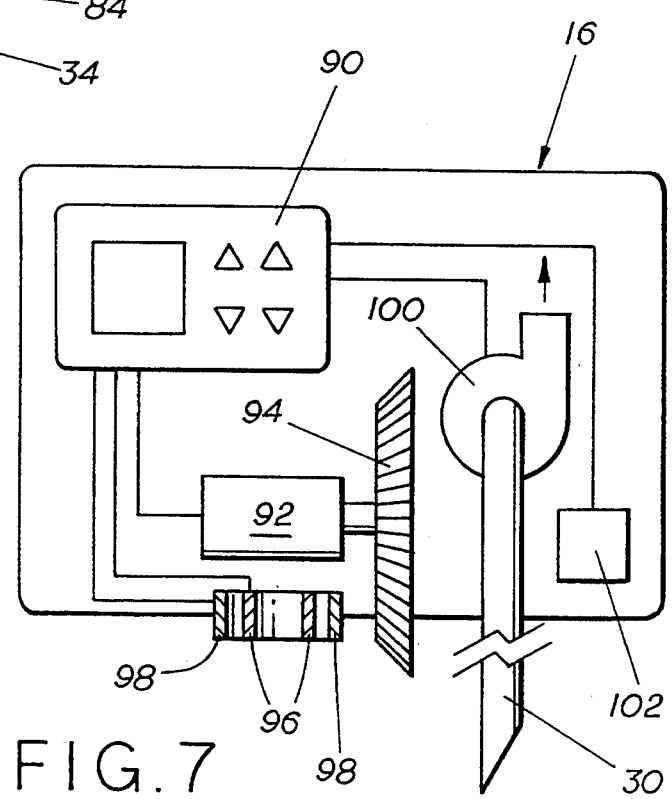
FIG.7

APPARATUS AND METHOD FOR MONITORING GASTRIC FLUID PH

FIELD OF THE INVENTION

The present invention pertains generally to medical diagnostic devices. More particularly, the present invention pertains to a device for monitoring pH values of the gastric contents of a patient. The present invention is particularly, but not exclusively, useful as an extracorporeal device with disposable components which aspirates the gastric contents of a patient for periodically monitoring the pH value of the patient's gastric contents while the patient is in a critical condition.

BACKGROUND OF THE INVENTION

A common problem associated with intensive care hospitalization is the development of gastric ulcers in patients who are substantially moribund. This condition effects thousands of patients each day, and it must be aggressively treated to prevent the development of ulcers in the gastric mucosa, that can lead to hemorrhage and death if not prevented. For many years, neutralizing agents consisting of hydrated magnesium or aluminum hydroxide were routinely instilled in the stomach. This method, although partially effective, was complicated and messy. Further, the neutralizer had to be instilled frequently, and the presence of the excess fluid in the stomach placed the patient at increased risk to aspiration of gastric contents into the lungs.

The discovery of a class of pharmaceutical agents known as $H_2$ antagonists has had a major impact on the prevention of stress related gastric mucosal damage (SRGMD) in critically ill patients. Proper use of these agents has been shown to effectively prevent the formation of stress related ulcers in a significant percentage of critically ill patients. However, acid production in the stomach is known to vary over time in each individual, and predicting when acid production is high, and how much antagonist an individual needs, is difficult. These agents, if given in a high dosage, can cause complete cessation of gastric acid production, in effect permitting the stomach to become a neutral environment which then can support the growth of pathogens. In the critically ill patient, aspiration of gastric contents into the lung occurs frequently, and several recent reports have shown an increase in pneumonia associated with the use of $H_2$ antagonists. Pneumonia in the critically ill patient is a life threatening condition. It is, therefore, imperative to monitor and control gastric fluid pH within therapeutically defined limits, to prevent a highly acidic condition, without promoting the growth of pathogens.

The intermittent monitoring of gastric pH is common in the practice of critical care medicine. This monitoring technique is focused on patients who are intubated with a nasogastric tube and who are critically ill. If their gastric pH is not controlled, up to 75% of these patients can develop significant SRGMD. The current method of monitoring pH consists of manually withdrawing a sample of gastric contents via the nasogastric tube and exposing the sample to litmus paper. Litmus paper develops color in relation to the pH of the applied sample, and the pH is estimated by comparing the color developed to the color of a calibration scale. Not only is this process time consuming and of limited accuracy, it also exposes the care giver to potentially hazardous material.

Electrochemical methods for determining pH have also been generally available for many years. These techniques involve the immersion of a sensor electrode, usually a pH sensitive glass, into the sample to be measured, along with a reference electrode to complete a measuring circuit. The electrode pair is calibrated before and after use by cleaning and exposing to solutions of known pH. Some of these electrochemical methods are known to exist for measuring gastric pH, involving the insertion of a miniature sensor directly into the stomach. Because of the risk and difficulty in placing such devices into the patient's gastrointestinal tract, the sensors must be of high quality and expensive construction, in order to minimize the effects of electrode drift over long periods of time.

Electrode drift is the time dependent change in the relationship between actual pH and the indicated pH. This is particularly important where gastric pH must be monitored over a 24 to 72 hour period. Even a relatively low drift rate for an in vitro sensor will be unacceptable, because of the length of the period of monitoring during which recalibration is not possible. At least one sensor designated to minimize this problem has a single crystal of antimony, prepared in a specific orientation on the tip of an electrode lead which can be inserted into a catheter. Miniature glass electrodes have also been utilized for in vitro sensing, but they are known to be fragile and subject to drift problems. Chemically sensitive field effect transistors and fiber optic photochemical sensors have also been developed for in vitro sensing.

In addition to the difficulty of having to frequently remove such endoscopic sensors for recalibration, their very design as miniature devices makes them better suited for determining pH at a local site, rather than as sensors for finding an average pH for the entire stomach. The production of acid is known to vary from site to site along the gastric mucosa, and as a consequence, the positioning of the in vivo sensor is critical to obtaining representative readings. Unfortunately, it is not possible to easily control the position of such catheters over several days of observation.

Although these teachings suggest great improvements can be obtained in measurement of gastric pH, they do not address how such complicated devices can be manufactured at a low cost and applied in a manner that gives a drift free, accurate, and representative average value of gastric pH that is appropriate for use in controlling gastric pH.

SUMMARY OF THE INVENTION

The preferred embodiment of the present invention is a device and method for monitoring the pH value of the gastric contents of a patient which includes a monitor, a sensor assembly, and a volume calibrated collecting reservoir. The sensor assembly is disposable and includes a sensor which is capable of generating a signal that is indicative of the pH value of a fluid.

A suction pump, mounted in the monitor housing of the device, is connected to the patient and is useable for aspirating gastric contents from the patient. A microprocessor, which is also mounted in the monitor housing, is electronically connected to the sensor of the sensor assembly to receive the pH value signal from the sensor. Consequently, when gastric contents are aspirated from the patient by the suction pump, and directed into contact with the sensor, the sensor will generate a signal that is indicative of the pH value of the gastric contents. This signal can then be recorded, and displayed as desired.

Periodically, during operation of the device, the sensor contacts a cleansing agent which removes gastric contents from the sensor. The cleansed sensor then sequentially contacts a plurality of reference solutions or standards, such as a pH 7 solution and a pH 1 solution. The signals generated by the sensor while in contact with the reference solutions are transmitted to the microprocessor where they are compared and used to calibrate the sensor for subsequent use. In this way, any operational errors which have developed in the system are eliminated.

For the preferred embodiment of the present invention, a volumetrically calibrated reservoir is attachable to the sensor assembly for collecting the aspirated gastric contents. In alternate embodiments of the present invention, the sensor can be either a metallic electrode, a field effect transistor, or a photo optical detector. Further, in an alternate embodiment of the present invention, the suction pump can be located externally from the monitor. Finally, the sensor can be moved into contact with cleansing and reference solutions in various different cavities, or the cleansing and reference solutions can be sequentially directed through a chamber which is in contact with the sensor.

BRIEF DESCRIPTION OF THE DRAWINGS

The novel features of this invention, as well as the invention itself, both as to its structure and its operation will be best understood from the accompanying drawings, taken in conjunction with the accompanying description, in which similar reference characters refer to similar parts, and in which:

FIG. 5 is a cross-sectional view of the disposable sensor assembly as seen along the line 5—5 in FIG. 3;

FIG. 6 is a cross-sectional view of the reservoir cap as seen along the line 6—6 in FIG. 2; and FIG. 7 is a schematic drawing of the components of the control assembly of the device of the present invention.

DESCRIPTION OF THE PREFERRED EMBODIMENT

Figure 1:
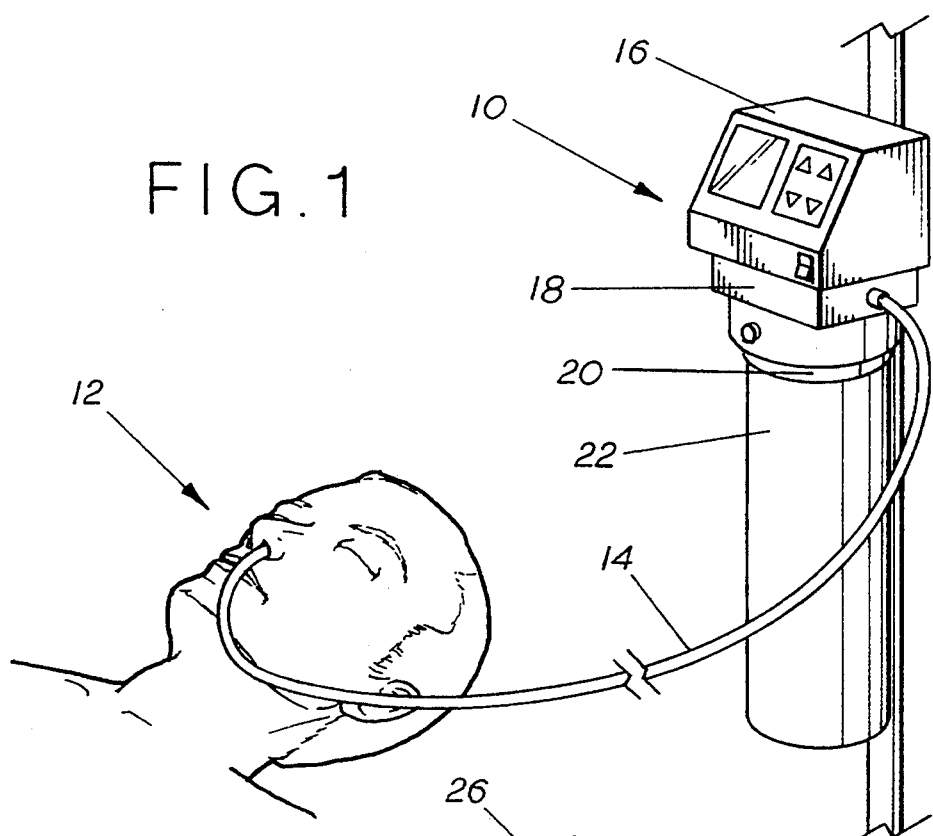
FIG. 1 is a perspective view of the pH monitoring device of the present invention shown operatively connected to a patient.

FIG. 1 shows the apparatus of the preferred embodiment of the present invention in use in its intended environment. The monitoring apparatus 10 of the present invention is operatively connected to the patient 12 via nasogastric tube 14. As will become apparent, this invention could just as well be used with other means of sampling gastric fluids, such as via an abdominal tube directly into the stomach. The monitoring apparatus 10 is shown hanging on a pole, but it could similarly be supported by several means. Power for monitoring apparatus 10 would preferably be via a power cord (not shown), but battery power could also be provided.

Figure 2:
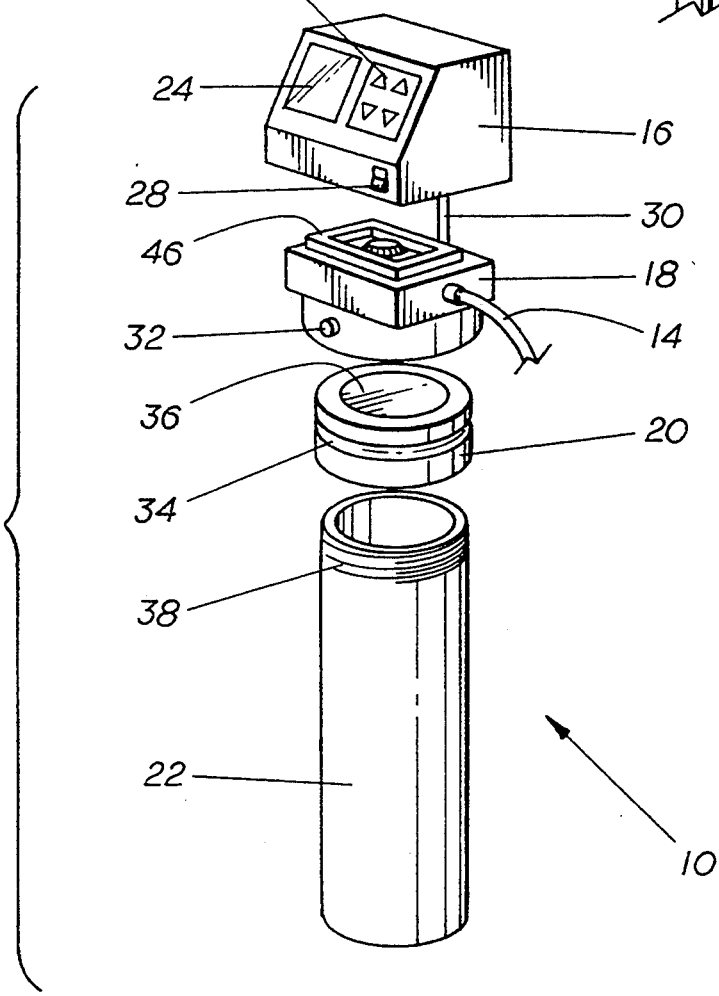
FIG. 2 is an exploded perspective view of the device.

As seen in FIG. 2, monitoring apparatus 10 consists of major components as follows: control assembly 16, disposable sensor assembly 18, reservoir cap 20, and gastric fluid reservoir 22. Sensor assembly 18 contains a pH sensor which can be selectively exposed to the gastric fluid or to a cleansing or calibration fluid. Control assembly 16 has a microprocessor which is programmed to operate a motor to selectively move the pH sensor, to receive signals from the pH sensor, to control a vacuum pump to aspirate gastric fluid from the patient, and to display pH information. Control assembly 16 also contains the necessary sensor motor and vacuum pump. Gastric fluid reservoir 22, which receives the gastric fluid aspirated from the patient, has threads 38 on its open end, to which reservoir cap 20 is threaded. Reservoir cap 20 is sealed across its top by self sealing septum 36, which can be a pierceable flexible membrane. Annular retaining groove 34 encircles the outside diameter of reservoir cap 20.

Disposable sensor assembly 18 is assembled on top of reservoir cap 20, and held in place by retaining plug 32, which can be a pliable elastomer shaped as an essentially cylindrical plug. Retaining plug 32 penetrates from the outside to the inside of sensor assembly 18 and projects into retaining groove 34 on reservoir cap 20, to hold sensor assembly 18 in place on reservoir cap 20.

Control assembly 16 is assembled on top of sensor assembly 18, and held in proper alignment by alignment ridge 46 on top of sensor assembly 18. Control assembly 16 is energized via power switch 28, and it can display such data as measured pH on display panel 24. Control of the operation of control assembly 16, and of the entire apparatus, is accomplished via control panel 26, which includes various switching devices well known in the art. Vacuum spike 30 projects downwardly from the bottom of control assembly 16 to penetrate self sealing septum 36, to draw a vacuum on reservoir 22, when the apparatus is assembled.

Figure 3:
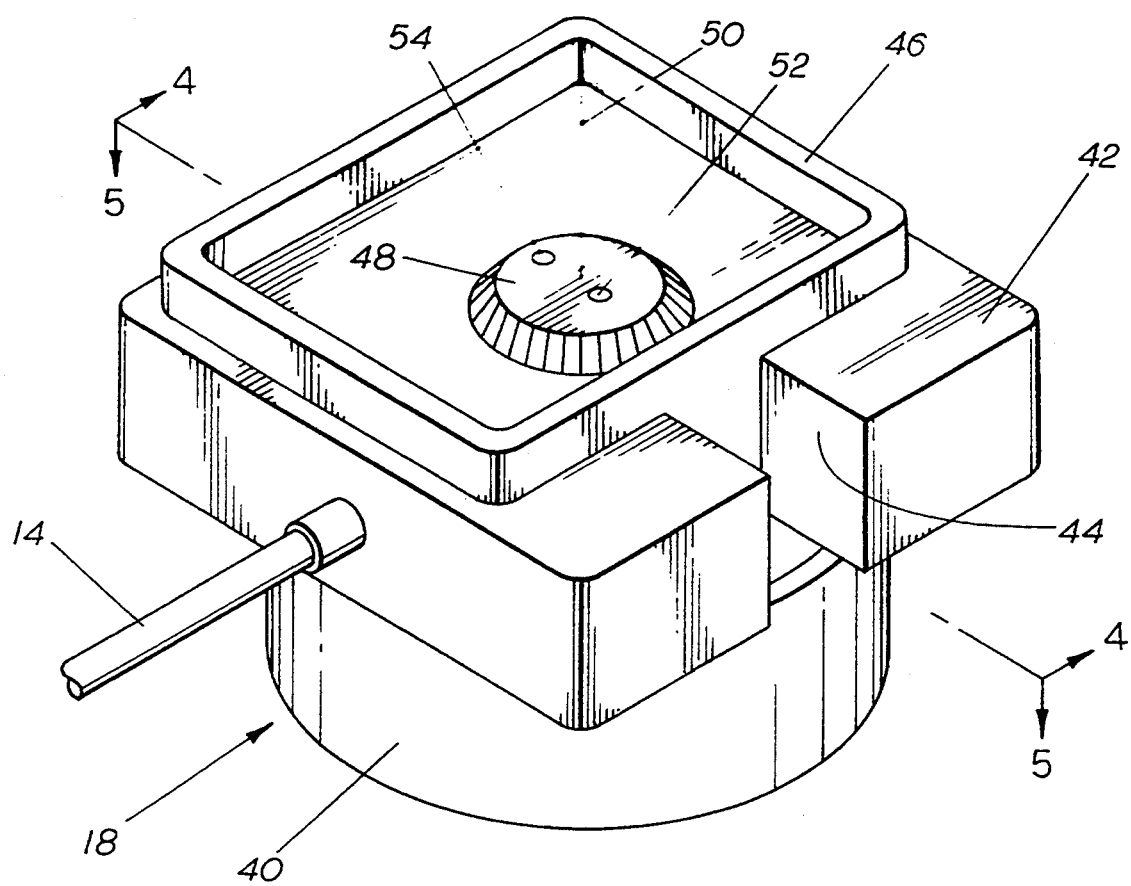
FIG. 3 is a perspective view of the disposable sensor assembly of the device.

FIG. 3 shows additional details of sensor assembly 18, which can be constructed as a disposable unit, facilitating repeated use of the control assembly 16. Sensor assembly 18 consists of three main structural parts, those being a body 42, a skirt 40, and an alignment ridge 46. Body 42 is a substantially solid, generally rectangular block having various internal cavities and ducts as will be explained later. Skirt 40 is a hollow cylinder attached to and projecting downwardly from body 42. Skirt 40 is shaped and sized to fit easily over the outside of reservoir cap 20, and it is held in place there by retaining plug 32. Alignment ridge 46 is an upwardly projecting ridge on top of sensor assembly 18 which can align with similar features on the bottom of control assembly 16, as is well known in the art, to establish and maintain the proper alignment between the interactive components of these two assemblies.

Also shown in FIG. 3 is access slot 44 extending completely through body 42 of sensor assembly 18, from top to bottom. Access slot 44 provides a path for vacuum spike 30 to pass through sensor assembly 18 to penetrate self sealing septum 36 on reservoir cap 20. Nasogastric tube 14 is attached to body 42 in fluid communication with several of the internal ducts in body 42. Sensor disk 48 is rotatably mounted on top of body 42, within alignment ridge 46. Sensor disk 48 is preferably in the shape of a bevel gear, having a plurality of gear teeth around its periphery. Alternatively, sensor disk 48 could be a friction wheel or some other type of power transmission means capable of selectively positioning sensing elements as will be explained later. Sensor contacts 52, 54 are exposed on top of sensor disk 48, to contact appropriate elements on the bottom of control assembly 16. Sensor contacts 52, 54 are arranged at two different distances from the centerline 50 of sensor disk 48. This allows sensor contact 52 to maintain electrical contact with a first contact ring on the bottom of control assembly 16, while sensor contact 54 maintains electrical contact with a second contact ring, as sensor disk 48 rotates about its centerline 50.

Figure 4:
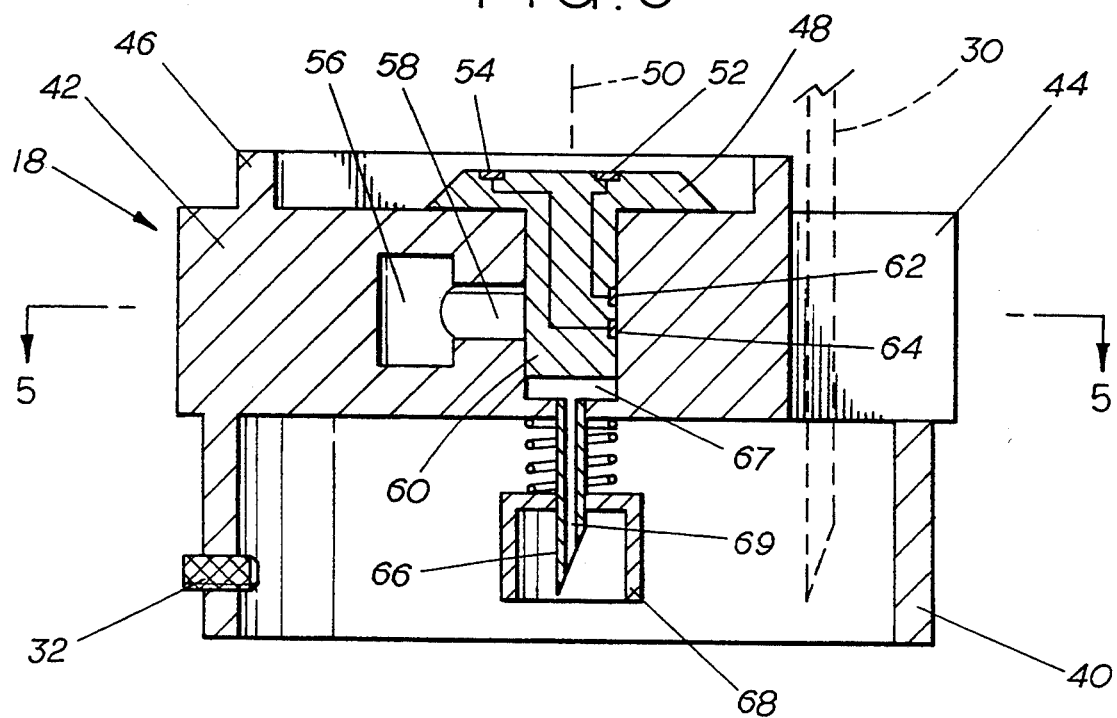
FIG. 4 is a cross-sectional view of the disposable sensor assembly as seen along the line 4—4 in FIG. 3.

FIG. 4 shows some of the internal details of sensor assembly 18, as a vertical section taken along the line 4—4 in FIG. 3. As explained above, sensor contact 52 is spaced from centerline 50 by a different distance than is sensor contact 54. When sensor disk 48 rotates about centerline 50, sensor contact 52 travels in a circle with a smaller diameter than the circle traveled by sensor contact 54. Solid, cylindrical sensor plug 60 is attached to and projects downwardly from sensor disk 48, with the same centerline. Electrical conductors run from sensor contacts 52, 54, down through sensor plug 60 to sensor electrodes 62, 64, respectively. Sensor electrodes 62, 64 are exposed on the outer surface of sensor plug 60, one above the other. Sensor plug 60 fits rotatably but in a fluid sealing fashion in sensor plug bore 67 in sensor assembly body 42. Sensor plug 60 is slightly shorter in length than the depth of sensor plug bore 67, leaving a fluid space at the bottom of sensor plug bore 67, connected to the lumen 69 through gastric fluid spike 66. The fluid space at the bottom of sensor plug bore 67 is also in fluid communication with nasogastric tube 14, as will be explained later.

Gastric fluid spike 66 is a sharp tube projecting downwardly from body 42, so as to pierce self sealing septum 36 when sensor assembly 18 is mounted on reservoir cap 20. Vacuum spike 30, shown in phantom in FIG. 4, projects downwardly from control assembly 16, through access slot 44 in sensor assembly 18, to pierce self sealing septum 36. Gastric fluid spike 66 is shown equipped with a cylindrical, spring biased spike shield 68, which surrounds spike 66 to prevent accidental sticks of operating personnel. Vacuum spike 30 will preferably be fitted with a similar shield, which is not shown, for the sake of clarity. As spike 66 or 30 pierces self sealing septum 36, its shield will be moved upwardly along the spike, against the force of its spring.

Calibration cavity 56 is a void in body 42, connected in fluid communication with sensor plug bore 67 by access duct 58. Calibration cavity 56 could have a variety of different shapes and still function as intended here, and it could be formed directly as an extension of sensor plug bore 67 instead of being connected by access duct 58. If necessary, calibration cavity 56 could be provided with agitation means to ensure that representative fluid is kept in contact with sensor plug 60. Calibration cavity 56 is representative in all respects of calibration cavity 70 and cleansing cavity 74, connected to sensor plug bore 67 by their access ducts 72, 76, respectively. Cavities 70 and 74 are shown in FIG. 5. Calibration cavity 56 is filled with a reference or calibration fluid having a pH, for example, of 7, and calibration cavity 70 is filled with a reference or calibration fluid having a pH, for example, of 1. Cleansing cavity 74 is filled with a cleansing fluid capable of cleansing gastric fluid from sensor electrodes 62, 64. As seen more clearly in FIG. 4, access ducts 58, 72, 76 are aligned vertically with sensor electrodes 62, 64, so as to expose both electrodes simultaneously to the fluid in a given access duct.

Also shown in FIG. 5 is gastric fluid inlet duct 78, passing horizontally through body 42 from nasogastric tube 14 to sensor plug bore 67. Gastric fluid passageway 80 exits the bottom of gastric fluid inlet duct 78, to connect with the fluid space in the bottom of sensor plug bore 67. This enables gastric fluid to flow through nasogastric tube 14 to gastric fluid inlet duct 78, on through passageway 80, through the fluid space in bore 67, and out through gastric fluid spike lumen 69 into reservoir 22. Sensor electrodes 62, 64 can be selectively aligned, by rotation of sensor plug 60, with gastric fluid duct 78, cleansing cavity 74, or one of the calibration cavities 56, 70. Sensor plug 60 seals against the wall of sensor plug bore 67, so as to prevent leakage from one of the calibration or cleansing cavities 56, 70, 74. Gastric fluid inlet duct 78 is always in fluid communication with gastric fluid spike 66 via sensor plug bore 67. The various cavities and ducts 56, 70, 74, 78 are arranged so that sensor electrodes 62, 64 can be exposed first to gastric fluid, then to cleansing fluid, then to pH 7 fluid, then to pH 1 fluid, for proper execution of the calibration sequence. Location of these cavities can be varied according to the particular sequence desired.

FIG. 6 shows reservoir cap 20, and the way in which gastric fluid spike 66 and vacuum spike 30 penetrate self sealing septum 36 when the apparatus of the present invention is assembled. Each spike 30, 66 is shown fitted with a spike shield 68, which has been pushed upwardly on its spike by contact with self sealing septum 36. Gastric fluid spike 66 penetrates essentially into the center of reservoir cap 20. Vacuum spike 30 penetrates into an annular channel formed between inner annular wall 82 and outer annular wall 84, which are rings projecting downwardly from self sealing septum 36. Annular microbiological filter 86 seals the open end of the annular channel between annular walls 82, 84, to prevent potentially hazardous microbes from being sucked out of reservoir 22 and released to the atmosphere. This filtered channel is formed in a ring on self sealing septum 36 to allow control assembly 16 to be mounted at any angular position relative to reservoir cap 20, ensuring that the resultant penetration of vacuum spike 30 will be within the microbe filtered channel.

FIG. 7 shows a schematic diagram of control assembly 16. Microprocessor 90 controls the electrical and mechanical equipment which positions the pH sensor electrodes, receives and analyzes their signal, and controls the vacuum equipment. Specifically, microprocessor 90 energizes disk rotating motor 92 to drive bevel shaped disk rotating gear 94, which meshes with and drives sensor disk 48. Rotation of sensor disk 48 selectively positions sensor electrodes 62, 64 to contact either gastric fluid, cleansing fluid, or one of the calibration fluids. Microprocessor 90 also controls vacuum pump 100, which draws a suction on vacuum spike 30 to draw a vacuum on reservoir 22, ultimately aspirating gastric fluid from the patient 12 via gastric fluid spike 66 and nasogastric tube 14. Vacuum pump 100 can be a piezoelectric pump designed to operate at frequencies above 25,000 hertz, to avoid the range of human hearing. Vacuum sensor 102 provides a vacuum level signal to microprocessor 90, to assist in control of vacuum pump 100. Microprocessor 90 can sense the signal from vacuum sensor 102 to maintain the vacuum in reservoir 22 at a predetermined level.

Finally, microprocessor 90 receives a voltage signal from inner sensor contact ring 96 and outer sensor contact ring 98, which microprocessor 90 analyzes and converts into a pH reading. Inner sensor contact ring 96 aligns with and contacts sensor contact 52 on sensor disk 48, regardless of the angular position of sensor disk 48. Similarly, outer sensor contact ring 98 aligns with and contacts sensor contact 54. Sensor contact rings 96, 98 or sensor contacts 52, 54 could be spring biased if desired, to ensure maintenance of proper sliding contact. Sensor electrodes 62, 64 act as a dual electrode pH sensor, as is well known in the art, and the signal from these electrodes is communicated to microprocessor 90 via sensor contacts 52, 54 and sensor contact rings 96, 98. The operation of microprocessor 90 is controlled through control panel 26, and microprocessor 90 displays information on display panel 24.

OPERATION

The operation of the apparatus of the present invention will now be described. Reservoir cap 20 is screwed onto reservoir 22. Disposable sensor assembly 18 is mounted on top of reservoir cap 20, pushing gastric fluid spike 66 through self sealing septum 36, and engaging retaining plug 32 with retaining groove 34. Control assembly 16 is mounted on top of sensor assembly 18, aligning with alignment ridge 46, and pushing vacuum spike 30 through self sealing septum 36.

Power switch 28 is activated, and the microprocessor 90 will display all segments of display panel 24, as a check. The microprocessor 90 will then simultaneously energize vacuum pump 100, to set a desired vacuum level in reservoir 22, and calibrate the pH sensor electrodes 62, 64. Calibration is accomplished by first rotating sensor disk 48 to position the electrodes 62, 64 to contact the cleansing fluid in cavity 74 long enough to cleanse the electrodes, then advancing the electrodes 62, 64 to contact the pH 7 fluid in cavity 56. When the voltage reading has stabilized, sensor disk 48 will be turned farther, to position the electrodes 62, 64 to contact the pH 1 fluid in cavity 70. When the voltage reading has stabilized, the microprocessor 90 will determine the pH vs. voltage curve, characteristic of the electrodes 62, 64, and quickly advance the electrodes 62, 64 to inlet duct 78.

Operating personnel can then check and adjust the vacuum setting, using the control panel 26, and connect the nasogastric tube 14 to the sensor assembly 18. Gastric fluid will then be aspirated through sensor assembly 18 and into reservoir 22. The control assembly 16 will measure and display the pH of the gastric fluid. Periodically, the control assembly 16 will cleanse and calibrate sensor electrodes 62, 64, to compensate for any drift that has occurred. The display panel 24 can display measured pH, vacuum level, and calibration status. The microprocessor 90 can also be connected to an audible alarm (not shown) to indicate various desired alarm conditions, such as low pH, high pH, or a full reservoir.

While the particular apparatus and method for monitoring gastric pH as herein shown and disclosed in detail are fully capable of obtaining the objects and providing the advantages herein before stated, it is to be understood that they are merely illustrative of the presently preferred embodiments of the invention and that no limitations are intended to the details of construction or design herein shown other than as described in the appended claims.

We claim:

1. A device for monitoring the pH value of the gastric contents of a patient which comprises:
   a body;
   a suction means for aspirating gastric contents from the patient to said body;
   a cavity on said body containing a cleansing fluid;
   a cavity on said body containing a calibration fluid;
   an extracorporeal sensor means for generating a signal indicative of the pH value of the aspirated gastric contents;
   means for selectively placing said sensor means in contact with one of said cavity containing said cleansing fluid to clean said sensor means, said calibration fluid to calibrate said cavity containing said sensor means, or the aspirated gastric contents to generate said signal; and
   electronic means connected to said sensor means for evaluating said signal to ascertain the pH value of the aspirated gastric contents.

2. A device for monitoring the pH value of the gastric contents of a patient which comprises:
   a sensor assembly formed with a cleansing cavity, at least one calibration cavity, and a monitoring cavity;
   a suction means for aspirating gastric contents from the patient into said monitoring cavity;
   an extracorporeal sensor mounted on said sensor assembly for generating a signal indicative of the pH value of the aspirated gastric contents;
   a disk mounted for rotation on said sensor assembly with said sensor being attached to said disk for rotation therewith;
   means for selectively rotating said disk to position said sensor in contact with one of said cleansing cavity, said calibration cavity or said monitoring cavity; and
   electronic means connected to said sensor for evaluating said signal to ascertain the pH value of the aspirated gastric contents.

3. A device as recited in claim 2 wherein said sensor assembly is formed with a first calibration cavity and a second calibration cavity, and wherein said first calibration cavity contains a pH 7 solution, and said second calibration cavity contains a pH 1 solution.

4. A device as recited in claim 3 wherein said electronic means comprises means for comparing a first signal form said sensor indicative of said pH 7 solution with a second signal from said sensor indicative of said pH 1 solution to calibrate said sensor.

5. A device as recited in claim 2 wherein said electronic means ia microprocessor.

6. A device as recited in claim 2 further comprising a collecting reservoir connected in fluid flow communication with said suction means for collecting the aspirated gastric contents after the gastric contents exit said monitoring cavity.

7. A sensor assembly for use in a system for monitoring the pH value of the gastric contents of a patient which comprises:
   a base member formed with a cleansing cavity, a calibration cavity, and a sample cavity;
   a sensor movably mounted on said base member, said sensor being capable of generating a signal indicative of the pH value of a sample fluid in contact with said sensor;
   means connected to said sensor for monitoring said signal to ascertain said pH value of said sample fluid; and
   means for selectively positioning said sensor in contact with one of said cleansing cavity to cleanse said sensor, said calibration cavity to calibrate said sensor, or said sample cavity to monitor said signal.

8. A sensor assembly as recited in claim 7 further comprising;

suction means connectable to said base member for aspirating gastric contents from the patient; and means for directing the aspirated gastric contents into contact with said sensor to generate said signal.

9. A sensor assembly as recited in claim 7 wherein said calibration cavity is a first calibration cavity and further comprising a second calibration cavity, and wherein said first calibration cavity contains a pH 7 solution, and said second calibration cavity contains a pH 1 solution.

10. A sensor assembly as recited in claim 9 wherein said monitoring means comprises means for comparing a first signal from said sensor indicative of said pH 7 solution in said first calibration cavity with a second signal from said sensor indicative of pH 1 solution in said second calibration cavity, to calibrate said sensor.

11. A sensor assembly as recited in claim 7 wherein said monitoring means is microprocessor.

12. A method for monitoring the pH value of the gastric contents of a patient which comprises the steps of:

providing an extracorporeal pH testing device, said extracorporeal device having a suction means for aspirating the gastric contents, a cavity containing cleansing fluid, a cavity containing calibration fluid, a sensor for generating a signal indicative of the pH value of the aspirated gastric contents, and an electronic means connected to said sensor for evaluating said signal to ascertain the pH value of the aspirated gastric contents;

inserting a nasogastric tube into the stomach of the patient;

connecting said nasogastric tube in fluid communication with a said suction means mounted on said an extracorporeal device to aspirate a stream of gastric contents from the patient;

selectively exposing said sensor to said cavity containing said cleansing fluid to clean said sensor;

selectively exposing said sensor to said cavity containing said calibration fluid to calibrate said sensor; and selectively exposing said sensor to the aspirated gastric contents to generate said signal.

13. A method as recited in claim 12 further comprising the steps of:

periodically cleansing said sensor;

sequentially subjecting said cleansed sensor to a pH 7 solution and to a pH 1 solution to respectively generate a first signal from said sensor and a second signal from said sensor; and transmitting said first signal and said second signal to said electronic means to calibrate said sensor.

14. A method as recited in claim 13 further comprising the step of attaching a reservoir to said extracorporeal device for collecting aspirated gastric contents after the gastric contents have been directed into contact with said sensor.

15. A method as recited in claim 12 wherein said sensor is a metallic electrode.

16. A method as recited in claim 12 wherein said sensor is a field effect transistor.

17. A method as recited in claim 12 wherein said sensor is a pH sensitive photo optical sensor.

18. A method as recited in claim 12 further comprising the steps of:

evaluating said signal to ascertain the pH value of the gastric contents; and displaying the pH value of the gastric contents.

* * * * *